United States Patent [19]

Dixon

[11] Patent Number: 4,911,704
[45] Date of Patent: Mar. 27, 1990

[54] MEDICATED HYGIENIC DEVICE

[76] Inventor: Wilbur Dixon, 44 S. Washington St., Beverly Hills, Fla. 32665

[21] Appl. No.: 300,380

[22] Filed: Jan. 23, 1989

[51] Int. Cl.⁴ .............................................. A61M 3/00
[52] U.S. Cl. ...................................... 604/83; 604/55; 604/279
[58] Field of Search ................. 604/39, 55, 73, 83–85, 604/257, 275, 279

[56] References Cited

U.S. PATENT DOCUMENTS

| | | | |
|---|---|---|---|
| 716,426 | 12/1902 | Jamison | 604/85 |
| 1,004,103 | 9/1911 | Tacey | 604/83 |
| 1,437,411 | 12/1922 | Fraser | 604/83 |
| 2,117,622 | 5/1938 | Morton et al. | 604/84 |
| 2,487,694 | 11/1949 | Capell | 604/84 |
| 2,722,933 | 11/1955 | Allen | 604/275 |
| 3,254,647 | 6/1966 | Vogel | 604/85 |
| 3,847,150 | 11/1974 | Scheuermann | 604/84 |
| 3,870,045 | 3/1975 | Vaughan | 604/84 |
| 4,000,742 | 1/1977 | DiGiacomo | 604/83 |
| 4,386,928 | 6/1983 | Hart | 604/83 |

Primary Examiner—Stephen C. Pellegrino
Assistant Examiner—Ralph Lewis
Attorney, Agent, or Firm—Merrill N. Johnson

[57] ABSTRACT

Apparatus attached to a shower head for cleansing parts of the body with a stream of medicated liquid. The apparatus includes a control valve assembly between the water supply pipe and the shower head and a flexible hose having one end connected to the control valve. The other end of the flexible tube lies within an elongated cylindrical mixing chamber with a small hole in the tube spaced from the end of the tube also lying within the mixing chamber. The forward end of the cylindrical mixing chamber is sealed by the swivelable ball-shaped end of a dispensing nozzle from which a mixture of water and medicant is discharged.

3 Claims, 1 Drawing Sheet

U.S. Patent | Mar. 27, 1990 | 4,911,704
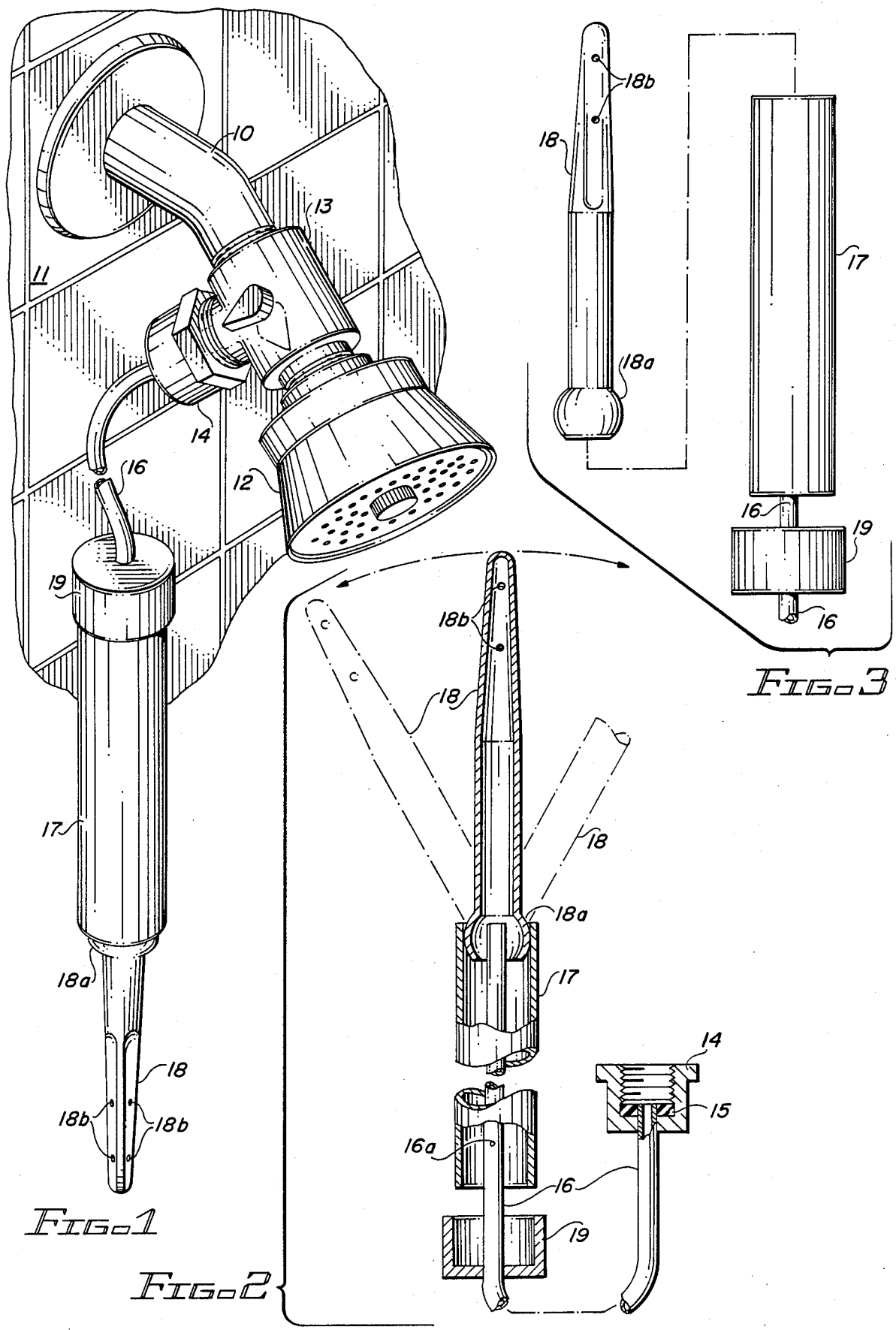

MEDICATED HYGIENIC DEVICE

BACKGROUND AND SUMMARY OF THE INVENTION

My invention relates generally to apparatus for cleansing parts of the body with a stream of medicated liquid, and more particularly to apparatus for irrigating and cleansing the vaginal cavity, which apparatus can be simply used in a conventional shower stall.

Various forms of apparatus for irrigating and cleansing the vaginal cavity with a medicated liquid are well known. In particular such apparatus designed for attachment to a shower head has been suggested as is apparent from U.S. Pat. Nos. 3,461,870; 3,512,525; 3,817,247 and 3,847,150. By attachment to a shower head, the user can easily adjust the temperature and pressure of the discharged liquid to the user's comfort and the liquid after use conveniently disappears into the shower drain.

However, so far as I am aware, all prior apparatus providing an antiseptic or medicated cleansing liquid requires the insertion of a cartridge of the medicant into the passageway leading to the nozzle of the apparatus, whereby the solid medicant is dissolved by water flowing through the medicant. This has the disadvantages of an ever changing concentration of medicant in the liquid delivered to the nozzle, frequent dissassembly of the apparatus to insert new medicated cartridges, and the expense of the cartridges themselves. Moreover, prior apparatus is both complicated and expensive to manufacture.

As opposed to hygienic apparatus which uses a solid cartridge to supply the antiseptic or medicant to the stream of liquid, my apparatus uses inexpensive liquids such as household vinegar. To properly mix the liquid medicant with water flowing from the shower pipe, my apparatus employs a unique mixing chamber whose forward end is sealed by the swivelable ball-shaped rear end of the dispensing nozzle.

Simply put, my apparatus includes a control valve assembly which is connected between a water supply pipe and a conventional shower head. A flexible tube or hose preferably made of ¼ inch diameter clear plastic material has one of its ends connected to the control valve through a restricted orifice of about 0.05 inches in diameter. The other end of the flexible tubing is contained within an elongated cylindrical mixing chamber. The forward end of the tubing terminates near the forward end of the mixing chamber and a small hole about 1/16th of an inch in diameter is punched into the wall of the tubing a short distance from the tubing's terminal end and lying near the rear end of the mixing chamber.

To prepare the apparatus for use, the dispensing nozzle is pulled out of the forward end of the mixing chamber. Holding the mixing chamber in a vertical position with its forward end uppermost, the desired liquid medicant or antiseptic such as vinegar is poured into the mixing chamber and then the chamber is sealed by reinsertion of the ball-shaped end of the dispensing nozzle.

By adjusting the shower faucet and opening the control valve, water at the desired temperature and pressure will flow through the restricted orifice and into the flexible tubing. A portion of the stream of water will be diverted through the 1/16th inch hole in the tubing to agitate the liquid medicant in the mixing chamber and blend with the water being fed into the dispensing nozzle from the terminal end of the flexible tube. Thus a cleansing stream of medicated water will be discharged from the dispensing nozzle at the desired temperature and pressure. The medicated stream will last from one to one and a half minutes before the supply of medicant has been exhausted.

BRIEF DESCRIPTION OF THE DRAWINGS

Without limiting the scope of my invention the appended drawings illustrate a preferred embodiment of my medicated hygienic device in which FIG. 1 is a perspective view partially broken away showing my device installed between a water supply pipe projecting from the wall of a conventional shower stall and a shower head, FIG. 2 is a side elevational view partially in cross-section of the medicated hygienic device shown in FIG. 1, and FIG. 3 is an exploded elevational view partially broken away of the mixing chamber and douche nozzle shown in FIGS. 1 and 2.

DETAILED DESCRIPTION OF THE PREFERRED EMBODIMENT

Referring to the drawings, in FIG. 1 a water pipe 10 projects from the tiled wall 11 of a conventional shower stall. Normally, shower head 12 would be directly connected to water pipe 10. My medicated hygienic device includes a two-way on-off control valve assembly 13 which is connected between pipe 10 and shower head 12 as shown in FIG. 1.

In addition to valve assembly 13, my device includes a coupling assembly connecting one end of a length of flexible tubing 16 to th rear end of an elongated cylindrical mixing chamber 17 and a douche or dispensing nozzle 18.

The coupling assembly includes internally threaded end cap 14, washer 15 and a restricted orifice between valve assembly 13 and tubing 16 having a diameter of about .05 inches which I have found will permit the flow of liquid from the dispensing nozzle at a rather constant rate despite changes in water pressure in supply line 10. Preferably end cap 14, mixing chamber 17, dispensing nozzle 18 and end cap 19 are made of plastic material such as polyvinyl chloride (PVC) or polystyrene both in interest of economy of manufacture and resistance to corrosion. The flexible tubing is preferably about five feet in length and ¼ inch in diameter and made of clear plastic material.

The open terminal end of tubing 16 lies at or near the forward end of mixing chamber 17, the rear end of which is closed by end cap 19. Mixing chamber 17 is an elongated cylinder having an internal capacity to hold about 2 ounces of liquid medicant. Mixing of the medicant with water flowing from supply pipe 10 is facilitated by a hole 16a having a diameter of 1/16th of an inch punched in the side of tubing 16 at a point near where the tubing passes through end cap 19 at the rear end of mixing chamber 17 as shown in FIG. 2. I have found that water flowing through hole 16a agitates the liquid medicant within chamber 17 and promotes quick and thorough mixing together of the water flowing through tubing 16 and the liquid medicant in chamber 17. At normal flow rates, it will take from one to one and a half minutes to mix and discharge all of the 2 ounces of medicant stored in mixing chamber 17.

The forward end of mixing chamber is sealed by the ball-shaped rear end 18a of dispensing nozzle 18. Being ball-shaped, the position of the nozzle can be simply changed by adjusting the angle between mixing chamber and nozzle, as is shown in FIG. 2 of the drawings.

Dispensing nozzle 18 is slightly tapered from its ball-shaped rear end 18a toward its tip with a plurality of dispensing holes 18b located to the rear of the nozzle's tip as best shown in FIGS. 1 and 3.

While I have shown a preferred embodiment of my medicated hygienic device, it should be understood that various changes and modifications may be made by those skilled in the art which fall within the spirit and scope of my invention, which is limited only by the following claims.

I claim:

1. Apparatus for attachment to a shower head for cleansing parts of the body with a stream of medicated liquid comprising an on-off valve assembly for connection between a water supply pipe and the shower head, an elongated cylindrical mixing chamber made of plastic material and for containing a medicated liquid, a flexible tube having its rear end connected to the control valve assembly and its open forward end extending through the mixing chamber and having a small cylindrical hole in the wall of the tube located within the mixing chamber and spaced rearwardly from the open forward end of the tube so that water flows both out of said small hole and the open forward end of the tube, and a dispensing nozzle made of plastic material having a ball shaped rear end dimensioned to fit snuggly into the front end of the cylindrical mixing chamber to seal the mixing chamber but permitting the nozzle to swivel on its ball shaped rear end within the mixing chamber.

2. Apparatus as set forth in claim 1 in which the mixing chamber has an internal capacity of two ounces.

3. Apparatus as set forth in claim 1 in which the connection between the control valve assembly and the rear end of the flexible tube includes a restrictive orifice having a diameter of about 0.05 inches through which water flows into the tube.

* * * * *